(12) United States Patent
Furman et al.

(10) Patent No.: US 8,911,090 B2
(45) Date of Patent: Dec. 16, 2014

(54) SYSTEM FOR AT-HOME EYE MOVEMENT MONITORING

(75) Inventors: Joseph M. Furman, Pittsburgh, PA (US); Mark S. Redfern, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 176 days.

(21) Appl. No.: 13/377,653

(22) PCT Filed: Jun. 30, 2010

(86) PCT No.: PCT/US2010/040523
§ 371 (c)(1),
(2), (4) Date: Feb. 15, 2012

(87) PCT Pub. No.: WO2011/002837
PCT Pub. Date: Jan. 6, 2011

(65) Prior Publication Data
US 2012/0133892 A1    May 31, 2012

Related U.S. Application Data

(60) Provisional application No. 61/221,735, filed on Jun. 30, 2009.

(51) Int. Cl.
*A61B 3/14* (2006.01)
*A61B 3/10* (2006.01)
*A61B 3/113* (2006.01)

(52) U.S. Cl.
CPC .. *A61B 3/113* (2013.01); *A61B 3/14* (2013.01)
USPC ........... 351/209; 351/158; 351/206; 351/221; 351/246

(58) Field of Classification Search
USPC ..................... 351/158, 41, 209–210
See application file for complete search history.

(56) References Cited

U.S. PATENT DOCUMENTS

| | | | |
|---|---|---|---|
| 4,659,197 A * | 4/1987 | Weinblatt | 351/210 |
| 5,886,822 A * | 3/1999 | Spitzer | 359/630 |
| 2004/0061831 A1 | 4/2004 | Aughey et al. | |
| 2005/0015120 A1 | 1/2005 | Seibel et al. | |
| 2006/0098087 A1 | 5/2006 | Brandt et al. | |
| 2007/0121068 A1 * | 5/2007 | MacDougall et al. | 351/221 |
| 2008/0049186 A1 | 2/2008 | MacDougall et al. | |
| 2009/0058660 A1 * | 3/2009 | Torch | 340/573.1 |
| 2010/0110368 A1 * | 5/2010 | Chaum | 351/158 |

OTHER PUBLICATIONS

The International Bureau of WIPO, "International Preliminary Report on Patentability and Written Opinion", Jan. 12, 2012, 6 pp.

* cited by examiner

*Primary Examiner* — Jordan Schwartz
(74) *Attorney, Agent, or Firm* — Eckert Seamans Cherin & Mellott, LLC; Stephen A. Bucchianeri

(57) ABSTRACT

An apparatus for monitoring eye movement in a patient, includes a frame structured to be worn on the head of the patient. An infrared illumination device structured to illuminate an eye of the patient is supported by the frame. A camera structured to capture images of the eye when illuminated by the infrared illumination device is also supported by the frame. A number of sensors structured to generate data relating to one or more characteristics of the user or environment is further supported by the frame. The apparatus also includes a data storage device associated with the frame for recording the images and the data relating to one or more characteristics of the user or environment along with time information associated therewith. The apparatus is structured to generally not obstruct the patient's view of their surroundings.

11 Claims, 3 Drawing Sheets

SYSTEM FOR AT-HOME EYE MOVEMENT MONITORING

CROSS-REFERENCE TO RELATED APPLICATION

This application claims priority under 35 U.S.C. §119(e) from U.S. Provisional Application No. 61/221,735, entitled "Goggles for At-Home Eye Movement Monitoring", which was filed on Jun. 30, 2009, the disclosure of which is incorporated herein by reference.

FIELD OF THE INVENTION

The present invention relates to changes in the eye, and more particularly, to an apparatus and method for monitoring and recording changes in the eyes of a patient.

BACKGROUND OF THE INVENTION

The presence of a number of medical and health problems can be detected by changes in the eye, including unusual changes in the position, movement and dilation of the eye. For example, it has been found that one of the leading causes of dizziness and balance problems is associated with the vestibular system in the inner ear. The presence of nystagmus (very specific, rapid, involuntary eye movements) during a dizziness attack can suggest to a clinician that there is a vertiginous component to it and the direction of the nystagmus may provide some evidence to a specialist in the field, of more specific information, such as which ear (or which part of the ear) has the active disease.

Dizziness and balance problems constitute a major public health problem. A significant proportion of adults have had an episode of dizziness that occurs with enough intensity or frequency to promote a visit to a physician. It is one of the most difficult complaints for a physician to assess, as dizziness is generally a subjective symptom of potentially numerous causes. Additionally, dizziness is often an episodic symptom, with the frequency of episodes highly variable. As a patient will very rarely have an episode while actually in the clinic, clinicians are frequently forced to rely solely on the patient's (often unintentionally misleading) report of the symptom(s).

Accordingly, accurate diagnosis of balance symptoms is important not only to exclude potentially serious central nervous system causes but to aid successful treatment. Unfortunately diagnosis is sometimes not possible, or is delayed. Studies have shown that general practitioners (GPs) rarely failed to refer urgent cases to specialists but often failed to refer patients with persistent vestibular conditions. Part of the difficulty is that the known apparatus for detecting and recording nystagmus and other eyes movements are large, expensive machines that are only available for use by specialists. Due to the size, complexity and expense of such machines, they are typically limited to laboratory use for specific tests. Such machines are rarely used to monitor patients at the time of a dizziness episode.

The present invention was developed with a view to providing a portable device for the investigation of eye movements that may occur during episodic vertigo and dizziness and a method of conducting the investigation using the device. The device can be used away from the clinic and does not need a specialist to operate it. However it will be understood that the device may also be used more generally in oculography and for investigation of the eye.

References to prior art in this specification are provided for illustrative purposes only and are not to be taken as an admission that such prior art is part of the common general knowledge.

SUMMARY OF THE INVENTION

In one non-limiting embodiment, the invention provides an apparatus for monitoring eye movement in a patient. The apparatus comprises: a frame structured to be worn on the head of the patient; an infrared illumination device supported by the frame, the infrared illumination device structured to illuminate an eye of the patient; a camera supported by the frame, the camera structured to capture images of the eye when illuminated by the infrared illumination device; a number of sensors supported by the frame, the number of sensors structured to generate data relating to one or more characteristics of the user or environment; and a data storage device associated with the frame for recording the images and the data relating to one or more characteristics of the user or environment along with time information associated therewith, wherein the apparatus is structured to generally not obstruct the patient's view of their surroundings.

The number of sensors may comprise a motion sensor, the motion sensor being structured to generate data relating to a position of the head. The number of sensors may comprise a luminance sensor for measuring data relating to ambient luminance. The number of sensors may comprise a motion sensor and a luminance sensor, the motion sensor being structured to generate data relating to a position of the head and the luminance sensor being structured to measure data relating to ambient luminance.

The camera may be adapted to capture the images at a frame rate of at least 60 Hz.

The frame may comprise a main portion and a pair of side portions, wherein the main portion comprises a reflective member supported thereon and wherein the camera is supported by one of the side portions and structured to capture images of the eye reflected by the reflective member.

The data storage device may be supported by the frame. The frame may comprise a transmitter supported thereon, the data storage device may be separated a distance from the frame, and the transmitter may be adapted to transmit the images and the data relating to one or more characteristics of the user or environment along with time information associated therewith to the data storage device for recording thereon.

The frame may comprise another camera supported thereon, the another camera being structured to capture images of the patient's surroundings.

In another non-limiting embodiment, the invention provides an apparatus for monitoring eye movement in a patient. The apparatus comprises: a frame structured to be worn on the head of the patient; an infrared illumination device supported by the frame, the infrared illumination device structured to illuminate an eye of the patient; a camera supported by the frame, the camera structured to capture images of the eye when illuminated by the infrared illumination device; a luminance sensor supported by the frame, the luminance sensor structured to generate data relating to the measured ambient luminance; and a data storage device associated with the frame for recording the images and the data relating to one or more characteristics of the user or environment along with time information associated therewith.

In a further non-limiting embodiment, the invention provides a method of diagnosing episodic occurrences of dizziness or vertigo in a patient using an apparatus. The apparatus comprises: a frame structured to be worn on the head of the patient; an infrared illumination device supported by the frame, the infrared illumination device structured to illuminate an eye of the patient; a camera supported by the frame, the camera structured to capture images of the eye when illuminated by the infrared illumination device; a number of sensors supported by the frame, the number of sensors structured to generate data relating to one or more characteristics of the user or environment; and a data storage device associated with the frame for recording the images and the data relating to one or more characteristics of the user or environment along with time information associated therewith, wherein the apparatus is structured to generally not obstruct the patient's view of their surroundings. The method comprises: providing the apparatus to the patient; receiving data recorded by the patient using the apparatus; and analyzing the data for the purpose of diagnosing a particular disorder or condition.

The data recorded may comprise images of the eye and data describing ambient luminance at the time the images of the eye were recorded, and analyzing the data may comprise analyzing both the images of the eye and the data describing the ambient luminance.

The method may further comprise: instructing the patient to don the apparatus when symptoms of at least one of dizziness and vertigo are experienced; and instructing the patient to perform at least one of a number of activities once the apparatus is donned by the patient. The number of activities may comprise: sitting upright in a lighted room; sitting upright in a darkened room; looking right, left, up, and down; lying supine in a dimly lit environment; and lying on a right and left side in a dimly lit environment.

BRIEF DESCRIPTION OF THE DRAWINGS

The accompanying drawings illustrate presently preferred embodiments of the invention, and together with the general description given above and the detailed description given below, serve to explain the principles of the invention. As shown throughout the drawings, like reference numerals designate like or corresponding parts.

DESCRIPTION OF THE PREFERRED EMBODIMENTS

Figure 1:
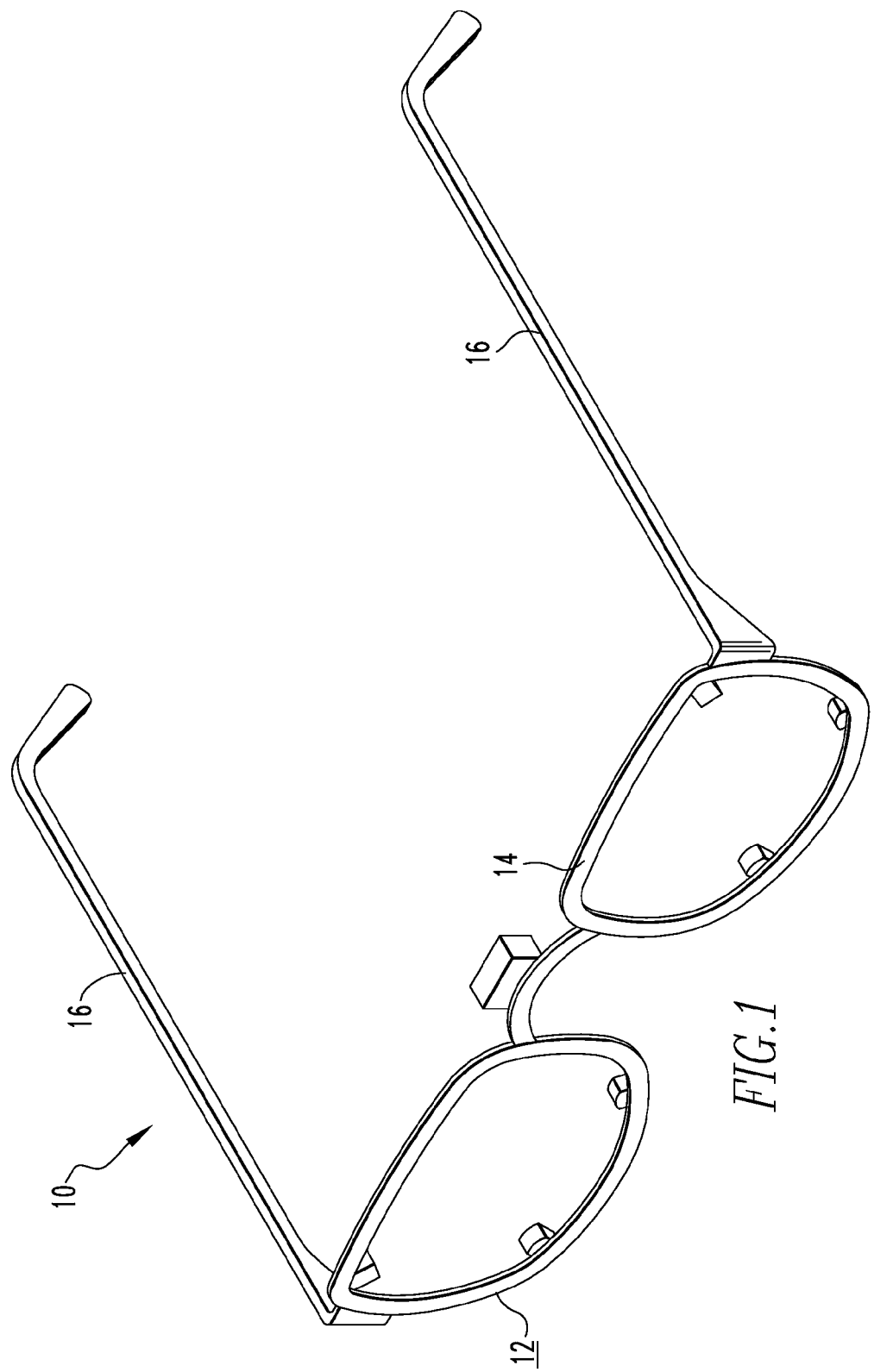
FIG. 1 is an isometric view of the front of an apparatus for monitoring eye movement in a patient according to an embodiment of the present invention.

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

As employed, herein, the statement that two or more parts or components are "coupled" together shall mean that the parts are joined or operate together either directly or through one or more intermediate parts or components.

As employed herein, the statement that a part or component "supports" another part or component shall mean that the second part or component may be coupled to, or otherwise generally mounted to, the first part or component.

As employed herein, the term "number" shall mean one or an integer greater than one (i.e., a plurality).

Figure 2:
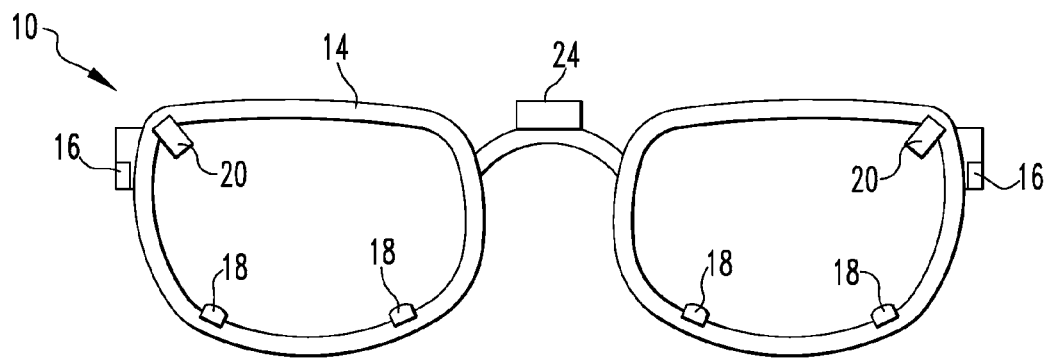
FIG. 2 is an elevation view of the rear of the apparatus of FIG. 1.
Figure 3:
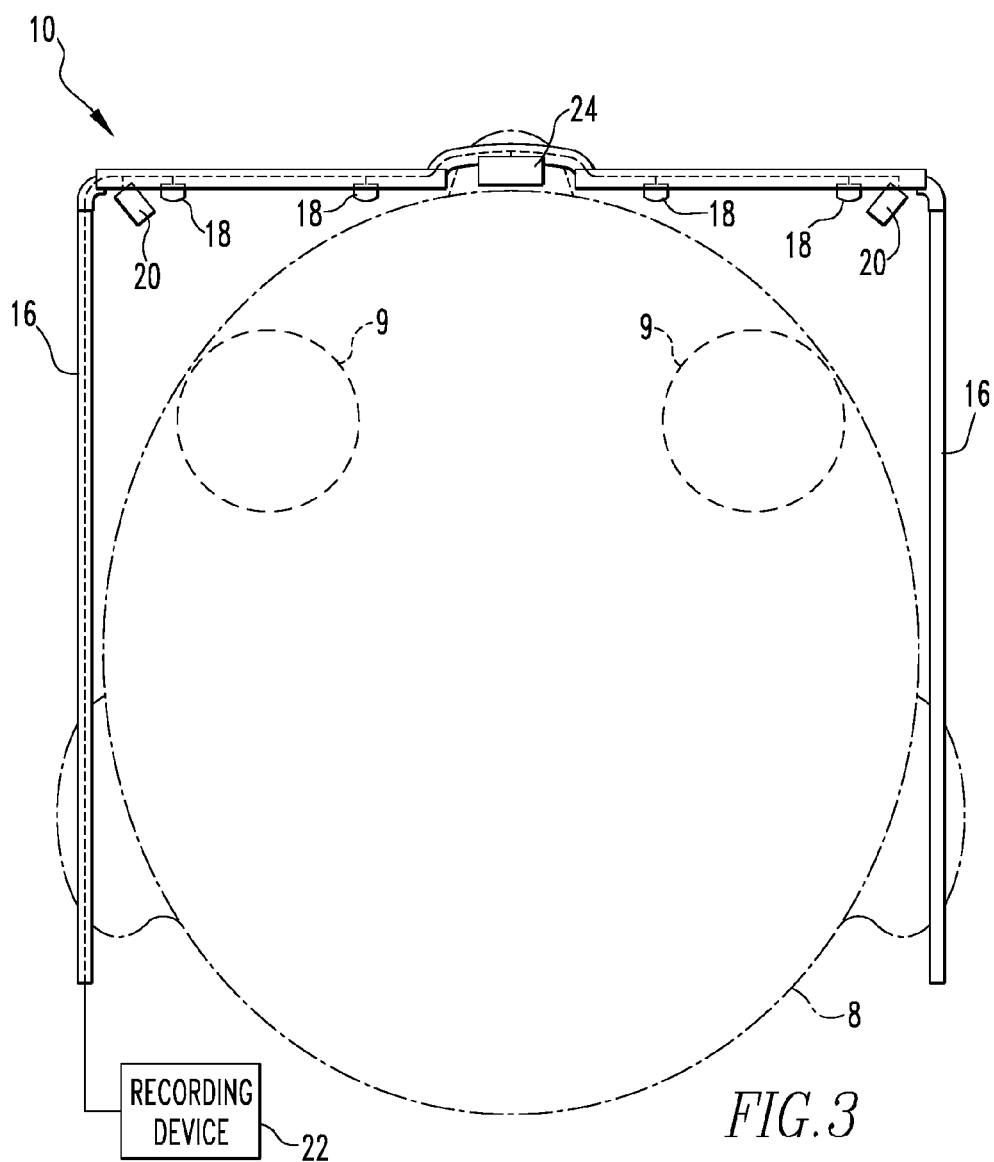
FIG. 3 is a plan view of the top of the apparatus of FIG. 1 positioned on the head of a patient.

FIGS. 1-3 show an apparatus 10 for monitoring eye movements in a patient according to an embodiment of the present invention. Apparatus 10 includes a frame assembly 12 that is adapted to be worn on the head 8 of a patient, such as depicted in the top view of FIG. 3. Preferably, frame assembly 12 is a lightweight, yet robust member formed from metal, plastic, or other suitable material. Although shown as essentially an eyeglass frame in FIGS. 1-3, it is to be appreciated that frame assembly 12 may comprise other suitable structures that may be readily fitted on or to the head of a patient at or about the patient's eyes.

Frame assembly 12 includes a main portion 14 and a pair of side portions 16. Main portion 14 is structured to generally be disposed in front of the eyes of a patient and rest on the patient's nose. Side portions 16 are structured to extend generally along either side of the patient's head and may slightly engage the patient's ears in order to help secure apparatus 10 to the patient's head. Side portions 16 may be integrally formed with main portion 14 or formed separately and either fixedly or pivotably coupled to main portion 14. Although not shown in FIGS. 1-3, apparatus 10 may further include a strap or other suitable mechanism to assist in securing apparatus 10 to a patient's head, preferably in a comfortable manner. As will be discussed further below, frame assembly 12 is adapted to support a number of monitoring components while generally not obstructing a patient's vision of their general surroundings. Accordingly, it is preferred that a patient may wear the apparatus 10 with similar comfort as a pair of reading glasses or sunglasses and be able to do basic activities (discussed further below) without being impeded by the apparatus 10.

FIG. 2 shows a rear view (the side which faces the patient) of the apparatus 10 that shows a number of the monitoring and related components supported by the frame assembly 12. Such components include a number of infrared light sources 18 supported on the frame assembly 12 for illuminating each of the eyes 9 of the patient. The embodiment shown in FIG. 2 includes four infrared light sources 18, two for each eye, coupled generally to a lower portion (not numbered) of main portion 14. The infrared light sources 18 may be light emitting diodes (LEDs) or other suitable infrared light sources supported on, or generally in, the frame assembly 12 and may include one or several for each eye. Continuing to refer to FIG. 2, a pair of cameras 20 are supported on the frame assembly 12, each camera being positioned to capture images of one of the patient's eyes when illuminated by the infrared light sources 18. Such cameras 20 may comprise any suitable imaging device capable of focusing and recording images of the patient's eyes. Important factors to be considered in choosing a suitable camera are focal length, sensor sizes, distance to image plane, image size and aperture (light). One particular preferable requirement of the lens mechanism (not numbered) of a camera 20 is to have a depth of field that will allow the eye image to be always in focus. As different users will have varying length between the lens and eye, the lens will usefully have a depth of field over this range. Another possibility is to employ a camera 20 employing auto-focusing technology or other focusing mechanism that may be adjusted by the patient and/or a clinician during an initial fitting.

In the example embodiment shown, each camera 20 employs a digital image sensor, currently CMOS or CCD technologies are suitable. Each image sensor typically includes a CCD sensor and controller and preferably include a lens incorporated into or attached thereto. The image sensors are operated to capture images at a predefined frame rate, preferably at least 60 Hz. The images of the patient's eye 9 captured by camera 20 may be processed to correct the images for such photographic problems as over-exposure or under-exposure, bad pixels, etc, prior to being stored on storage/recording device 22, which is in communication with each of the cameras 20. Storage/recording device 22 may be of any suitable storage means capable of storing a quantity of digital images and other electronic information and preferably has a storage capacity that can accommodate at least one hour of recorded images and other data in a format that can be easily transferred to a desktop computer. Storage/recording device may be supported on, and/or integrated with, the frame assembly 12. In such arrangement, storage/recording device 22 is preferably electrically coupled to each of the cameras 20 via wiring. Although not shown in the FIGS., it is to be appreciated that storage/recording device 22 may also be separate from the frame assembly 12. In such application, a suitable transmitter is further provided on the frame assembly 12 for wirelessly transmitting image and other signals from the frame assembly to the storage/recording device 22.

Referring to FIGS. 2 and 3, the apparatus 10 preferably includes a number of sensors 24 supported by frame assembly 12 and in communication with recording device 22 for generating and storing data relating to one or more characteristics of the user and/or the environment. For example, a motion sensor may be provided on frame assembly 12 for detecting the relative position of the patient's head and generating data regarding such positioning. Such data are recorded on recording device 22. As another example, a luminance sensor may also be provided for measuring data related to ambient luminance. Such characteristics of the user and environment are important to record as they may have a causal relationship on the symptoms experienced by the patient or the patient's eye movements. As a further example, a third camera may be provided to capture images of the patient's surroundings.

Figure 4:
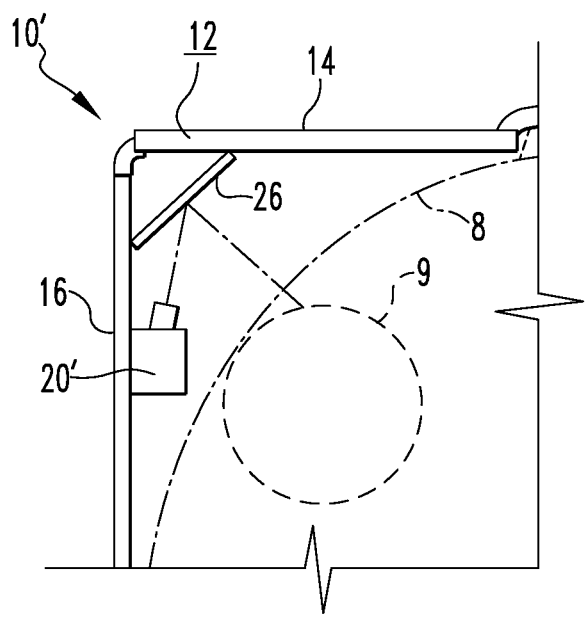
FIG. 4 is a top view of a portion of an apparatus for monitoring eye movement in a patient according to another embodiment of the present invention.
Figure 5:
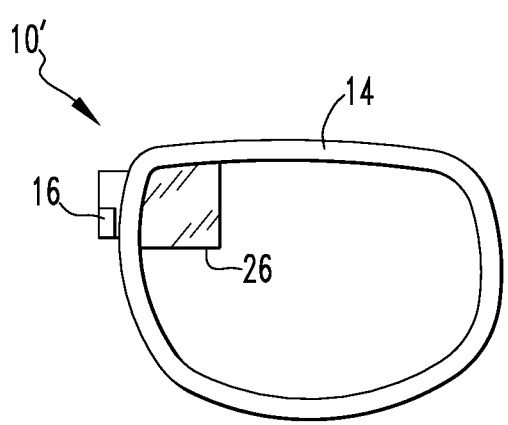
FIG. 5 is an elevation view of the rear of the portion of the apparatus shown in FIG. 4.

FIGS. 4 and 5 show top and rear views of a portion of an apparatus 10' for monitoring eye movements in a patient according to another embodiment of the present invention. Like apparatus 10 previously discussed, apparatus 10' includes a frame assembly 12 having a main portion 14 and a pair of side portions 16. However, unlike the previously discussed apparatus 10, which utilized cameras 20 aimed directly at each of the patient's eyes, the apparatus 10' of FIGS. 4 and 5 utilizes a camera 20 for each eye that is generally supported on the side portion 16 and relies on a reflective member 26, such as a small mirror, to reflect images of the eye which are captured by camera 20', and subsequently transmitted to a recording device 22, as discussed in connection with the embodiment shown in FIGS. 1-3. Such arrangement allows for the use of a generally larger camera 20' or for a camera 20' having a relatively longer focal distance.

As such it is to be appreciated that the present invention provides a relatively compact apparatus that may be worn by a patient during many normal daily activities or that may be readily donned by a patient when symptoms of dizziness or vertigo are first sensed. Accordingly, it is envisioned that the apparatus would be "loaned" to a patient on a temporary basis by a prescribing physician. The apparatus thus would allow a patient to record their eye movements during episodes of dizziness and vertigo, wherever such episodes may occur.

Eye position is then computed off-line, prior to analysis by an expert physician. Other potential causal elements, such as time of day, ambient luminance, and head position are also recorded and correlated with the images of the eyes for analysis by the expert physician. Such recorded data will then enable physicians to evaluate physiologic data collected during attacks of dizziness and vertigo and thereby improve the diagnostic accuracy, and thus treatment of many common balance disorders.

In a preferred use of the apparatus 10, a patient dons the apparatus 10 when they first feel the symptoms of dizziness or vertigo. Once donned, the patient then performs several simple maneuvers such as: sitting upright in a lighted room; sitting upright in a darkened room; looking right, left, up, and down; lying supine in a dimly lit environment; and lying on their right and left side in a dimly lit environment. The images of the eye are then processed using image analysis software to generate a record of horizontal, vertical and torsional eye position versus time with an accompanying record of time of day, ambient luminance, and head position with respect to gravity. Such data is then analyzed by an ordering physician along with the video images of the eye movements and incorporated into the diagnostic process.

While preferred embodiments of the invention have been described and illustrated above, it should be understood that these are exemplary of the invention and are not to be considered as limiting. Additions, deletions, substitutions, and other modifications can be made without departing from the spirit or scope of the present invention. Accordingly, the invention is not to be considered as limited by the foregoing description but is only limited by the scope of the appended claims.

What is claimed is:

1. An apparatus for monitoring eye movement in a patient, the apparatus comprising:
   a frame structured to be worn on the head of the patient;
   an infrared illumination device supported by the frame, the infrared illumination device structured to illuminate an eye of the patient;
   a camera supported by the frame, the camera structured to capture images of the eye when illuminated by the infrared illumination device;
   a luminance sensor structured to measure ambient luminance supported by the frame, the luminance sensor structured to generate data relating to the measured ambient luminance; and
   a data storage device associated with the frame for recording the measured ambient luminance and for recording the images and additional data relating to one or more characteristics of the patient or environment along with time information associated with the measured ambient luminance, the recorded images and the additional data;
   wherein the apparatus is structured to generally not obstruct the patient's view of their surroundings.

2. The apparatus according to claim 1, further comprising a number of sensors supported by the frame, the number of sensors structured to generate data relating to one or more characteristics of the patient or environment.

3. The apparatus according to claim 2, wherein the number of sensors comprises a motion sensor, the motion sensor being structured to generate data relating to a position of the head.

4. The apparatus according to claim 2, wherein the camera is adapted to capture the images at a frame rate of at least 60 Hz.

5. The apparatus according to claim 2, wherein the frame comprises a main portion and a pair of side portions, wherein the main portion comprises a reflective member supported thereon, and wherein the camera is supported by one of the side portions and structured to capture images of the eye reflected by the reflective member.

6. The apparatus according to claim 2, wherein the data storage device is supported by the frame.

7. The apparatus according to claim 2,
wherein the frame comprises a transmitter supported thereon;
wherein the data storage device is separated a distance from the frame; and
wherein the transmitter is adapted to transmit, and the data storage device is adapted to receive and record, the images and the data relating to one or more characteristics of the patient or environment along with time information associated therewith.

8. The apparatus according to claim 2, wherein the frame comprises another camera supported thereon, the another camera being structured to capture images of the patient's surroundings.

9. A method of diagnosing episodic occurrences of dizziness or vertigo in a patient using an apparatus comprising: a frame structured to be worn on the head of the patient; an infrared illumination device supported by the frame, the infrared illumination device structured to illuminate an eye of the patient; a camera supported by the frame, the camera structured to capture images of the eye when illuminated by the infrared illumination device; a number of sensors supported by the frame, the number of sensors structured to generate data relating to one or more characteristics of the user or environment; a luminance sensor supported by the frame, the luminance sensor structured to generate data relating to the measured ambient luminance; and a data storage device associated with the frame for recording the measured ambient luminance and for recording the images and additional data relating to one or more characteristics of the patient or environment along with time information associated with the measured ambient luminance, the recorded images and the additional data, wherein the apparatus is structured to generally not obstruct the patient's view of their surroundings, the method comprising:
providing the apparatus to the patient;
instructing the patient to don the apparatus when symptoms of at least one of dizziness and vertigo are experienced;
instructing the patient to perform at least one of a number of activities once the apparatus is donned by the patient;
receiving data recorded by the patient using the apparatus; and
analyzing the data for the purpose of diagnosing a particular disorder or condition.

10. The method according to claim 9, wherein the data recorded comprises images of the eye and data describing ambient luminance at the time the images of the eye were recorded, and wherein analyzing the data comprises analyzing both the images of the eye and the data describing the ambient luminance.

11. The method according to claim 9, wherein the number of activities comprise: sitting upright in a lighted room; sitting upright in a darkened room; looking right, left, up, and down; lying supine in a dimly lit environment; and lying on the right and left side in a dimly lit environment.

* * * * *